United States Patent [19]

Neustadt et al.

[11] Patent Number: 4,559,340

[45] Date of Patent: Dec. 17, 1985

[54] ANTIHYPERTENSIVE AGENTS

[75] Inventors: Bernard R. Neustadt, West Orange; David R. Andrews, Bloomfield; Paul E. McNamara, Westfield, all of N.J.

[73] Assignee: Schering Corporation, Kenilworth, N.J.

[21] Appl. No.: 555,311

[22] Filed: Nov. 25, 1983

[51] Int. Cl.[4] .................... C07D 417/12; A61K 31/54
[52] U.S. Cl. ........................................ 514/222; 544/6; 544/13; 260/243.3; 260/112.5 R
[58] Field of Search .................. 544/13, 6; 260/243.3, 260/112.5 R; 424/246; 514/222

[56] References Cited

U.S. PATENT DOCUMENTS

| | | | |
|---|---|---|---|
| 4,338,435 | 7/1982 | Haugwitz | 544/12 |
| 4,431,645 | 2/1984 | Smith et al. | 544/13 |
| 4,468,396 | 8/1984 | Magatti | 544/13 |

OTHER PUBLICATIONS

Abstract of European Patent Application 95584, Dec. 1983.
Abstract of Australian Patent Application 8, 313,837, Nov. 1983.

*Primary Examiner*—John M. Ford
*Attorney, Agent, or Firm*—Anita W. Magatti; Stephen I. Miller

[57] ABSTRACT

There are disclosed benzothiadiazinyl and quinazolinyl substituted carboxylalkyl dipeptides, wherein the benzothiodiazinyl or quinazolinyl portions are joined to the dipeptide portions by an aminocarbonyl group. Compounds of this invention are useful as antihypertensive agents, in the treatment of congestive heart failure and in the treatment of glaucoma. In addition, compounds of this invention have diuretic activity.

18 Claims, No Drawings

ANTIHYPERTENSIVE AGENTS

SUMMARY

The present invention relates to benzothiadiazinyl and quinazolinyl substituted carboxyalkyl dipeptides, wherein the benzothiodiazinyl or quinazolinyl portions are joined to the dipeptide portions by an aminocarbonyl group. Compounds of this invention are useful as antihypertensive agents, in the treatment of congestive heart failure and in the treatment of glaucoma. In addition, compounds of this invention have diuretic activity.

DETAILED DESCRIPTION

More particularly, this invention relates to compounds represented by the following formulae:

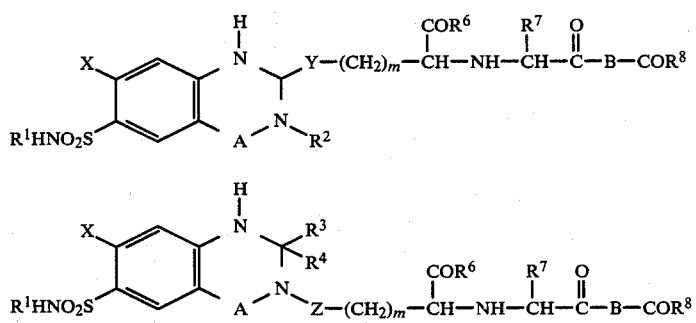

wherein
A is $-SO_2-$ or

X is Cl or $CF_3$;
Y is

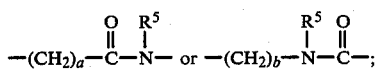

Z is

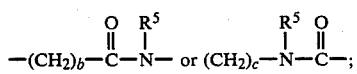

B is

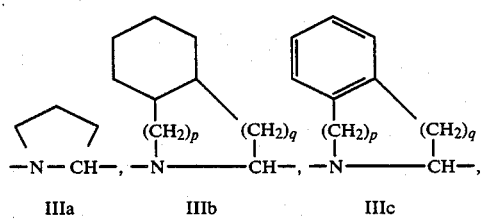

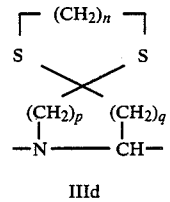

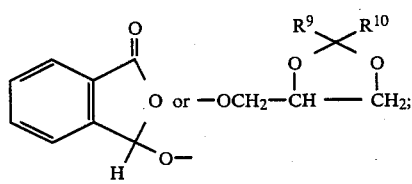

$R^1$ is hydrogen or lower alkyl;
$R^2$ and $R^5$ are independently hydrogen, lower alkyl, phenyl, or phenyl(lower)alkyl;
$R^3$ and $R^4$ are independently hydrogen, lower alkyl, haloloweralkyl, phenyl, or phenyl(lower)alkyl, or $R^3$ and $R^4$ taken together with the carbon to which they are attached can form a 5–7 membered cycloalkyl ring;
$R^6$ and $R^8$ are independently hydroxy, alkoxy having from 1 to 8 carbon atoms, $L-Q_r-(CH_2)_s-O-$, wherein L is phenyl, substituted phenyl, 1-naphthyl or 2-naphthyl; Q is oxygen or sulfur; r is 0 or 1 and s is 0 to 4; and wherein the substituents on the phenyl are chosen from group M, wherein M is halogen, hydroxy, trifluoromethyl, alkoxy having from 1 to 6 carbon atoms, alkyl from 1 to 6 carbon atoms, 2-furanyl, 3-furanyl, 2-thienyl, 3-thienyl and phenyl (which phenyl group may be substituted with halogen, hydroxy, trifluoromethyl, alkoxy having from 1 to 6 carbon atoms or alkyl having from 1 to 6 carbon atoms); provided that when s is zero, r is zero; $-OCH_2-OCO$-alkyl wherein the alkyl has from 3 to 8 carbon atoms, $-OCH_2CO$-phenyl, wherein the phenyl may be substituted with group M, 1-gylceryl, $R^7$ is hydrogen, lower alkyl, or aminoloweralkyl;
$R^9$ is hydrogen, lower alkyl, unsubstituted or substituted phenyl, and substituted or unsubstituted phenyl lower alkyl, wherein phenyl may be substituted by group M;
$R^{10}$ is hydrogen or lower alkyl;
a is 0–8;
b is 1–8;
c is 2–8;

m is 1-4;

n is 0 or 1;

p and q are each 0, 1 or 2, provided that in formulae IIIb and IIIc the sum of p and q is 1 or 2, and that in formula IIId, p is not 0; and pharmaceutically acceptable salts thereof.

When B is formula IIIb or IIIc, the preferred sum of p and q is 1; when B is of formula IIId, preferred values for each of p and q are 1.

For compounds of formula I wherein Y is

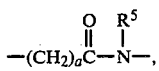

preferred compounds are those wherein m is 3 or 4. For compounds of formula I wherein Y is

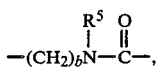

preferred compounds are those wherein m is 1 or 2. Also preferred are compounds wherein $R^7$ is hydrogen, methyl or aminobutyl, compounds wherein $R^1$ and $R^2$ are hydrogen or methyl, compounds wherein X is chlorine, and compounds wherein $R^6$ is hydroxy, ethoxy, methoxy, phenoxyethoxy, pivaloyloxymethoxy, or

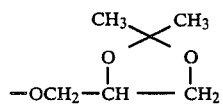

As used herein, "lower alkyl" means straight or branched chain hydrocarbon radicals of from 1 to 6 carbons, e.g. methyl, ethyl, propyl, isopropyl, butyl, t-butyl, pentyl and hexyl. Similarly, "lower alkoxy" means straight or branched alkoxy radicals having 1 to 6 carbon atoms, e.g. methoxy, ethoxy, propoxy, butoxy, iso-butoxy, pentoxy and hexyloxy. "Halogen" means fluorine, chlorine and bromine.

Compounds of the instant invention include various stereoisomers. Preferred stereoisomers are those in which the absolute configuration at each of the three carbon atoms adjacent to both a nitrogen and a carbonyl group corresponds most closely to the absolute configuration of L-amino acids.

The compounds of this invention form salts with various inorganic and organic acids and bases which are also within the scope of the invention. Such salts include ammonium salts, alkali metal salts, e.g. sodium and potassium salts, and alkaline earth metal salts, e.g. calcium and magnesium salts. Salts with organic and inorganic acids may be prepared, e.g., HCl, HBr, $H_2SO_4$, $H_3PO_4$, methanesulfonic acid, toluenesulfonic acid, maleic acid, fumaric acid and camphorsulfonic acid. The non-toxic pharmaceutically acceptable salts are preferred, although other salts are also useful, e.g., in isolating or purifying the product. The acid salts (e.g. HCl and maleate) are preferred, especially the hydrochloride.

The salts may be formed by conventional means, as by reacting the free acid or base forms of the product with one or more equivalents of the approrpriate base or acid in a solvent or medium in which the salt is insoluble, or in a solvent such as water which is then removed in vacuo or by exchanging the cations of an existing salt for another cation on a suitable ion exchange resin.

Compounds of formulae I and II may be prepared by several routes using methods known in the art.

For example, compounds of formula I can be prepared by condensing an acid of formula IV with an amino acid of formula V:

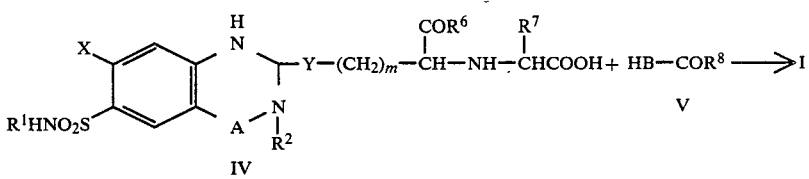

wherein $R^1$, $R^2$, $R^6$, $R^7$, A, B, X, Y and m are as defined above. The reaction is carried out in an inert solvent such as dimethylformamide (DMF) in the presence of a base such as triethylamine and a condensing agent such as 1-(3-dimethylaminopropyl)-3-ethyl carbodiimide hydrochloride (DEC) and 1-hydroxybenzotriazole. The reaction is preferably carried out in an inert atmosphere at a temperature of 0°-25° C.

Compounds of formula IV wherein Y is

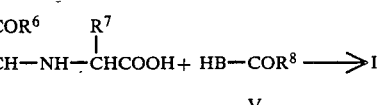

(acylamide type) can be prepared from the reaction of an acid of formula VI and benzothiadiazine or quinazoline of formula VII:

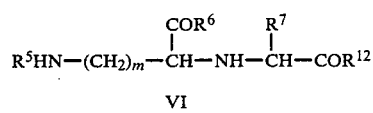

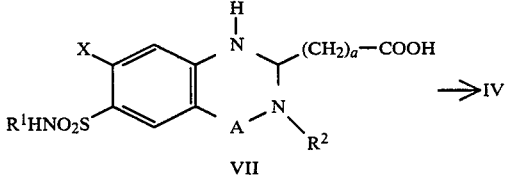

wherein A, X, $R^1$, $R^2$, $R^5$, $R^7$, a and m are as defined above and $R^{12}$ is a readily removable ester protecting group such as t-butyl or benzyl. The reaction conditions are similar to those described above for the preparation of compounds of formula I.

Compounds of formula VI are either known in the art or may be prepared by well known procedures, for example by the reaction of an N-protected diaminoacid of formula VIII with an ester of formula IX, followed by removal of the N-protecting group:

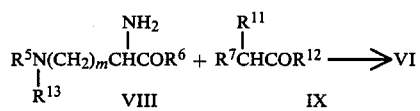

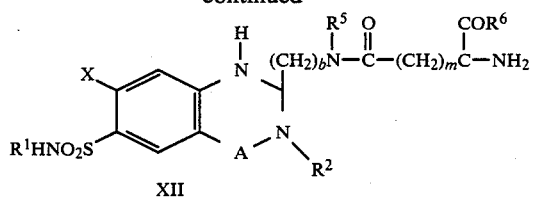

wherein R⁵, R⁶, R⁷, R¹² and m are as defined above and R¹¹ is a leaving group such as chlorine, bromine arylsulfonyloxy, alkylsulfonyloxy or trifluoromethanesulfonyloxy, and R¹³ is an N-protecting group such as benzyloxycarbonyl (CBZ) or t-butyloxycarbonyl (BOC). The reaction is carried out at room temperature or elevated temperatures (70°–90° C.) in an inert solvent such as DMF in the presence of a base such as triethylamine. The N-protecting group R¹³ can then be selectively removed by suitable conventional methods, e.g. when R¹² is t-butyl and R¹³ is CBZ, catalytic hydrogenation can be used to selectively remove the CBZ group.

wherein A, R¹, R², R⁵, R⁶, R¹³, X, b and m are as defined above. The N-protecting group may be selectively removed by a suitable reagent, e.g. a preferred R¹³ group for compounds of formula X is BOC, which can be removed by treatment with hydrochloric acid in dioxane. The amino acid of formula XII may be then treated with an ester of formula IX to produce compounds of formula IVa:

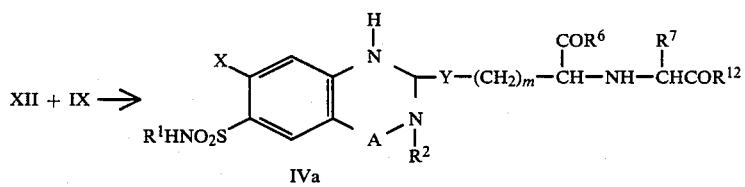

Compounds of formula IV wherein Y is

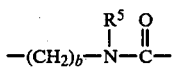

(alkylamino carbonyl type) can be prepared by reacting an acid of formula X with a benzothiadiazine or quinazoline of formula XI, then selectively removing the N-protecting R¹³ group:

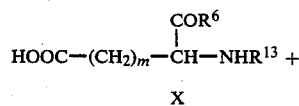

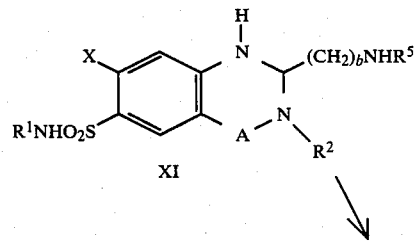

The ester group R¹² can then be removed by conventional methods to yield a compound of formula IV, e.g. a t-butyl group can be removed by treating with hydrochloric acid in dioxane.

Use of esters of formula IX wherein R¹¹ is a triflate group to prepare a single diastereomer of an amino acid ester is disclosed in copending U.S. Ser. No. 500,494 filed June 2, 1983. The reaction is carried out at room temperature in an inert solvent such as ethyl acetate in the presence of a base such as triethylamine.

Compounds of formula II can be prepared from intermediates analogous to those used in preparing compounds of formula I in a procedure as described for formula I. For example, an acid of formula XIV can be condensed with an amino acid of formula V:

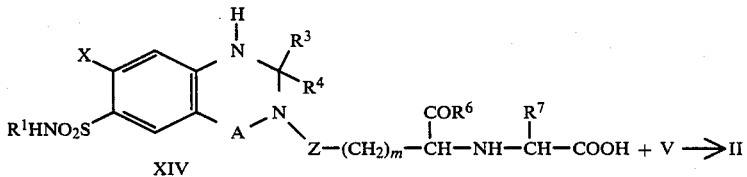

wherein A, X, Z, R¹, R³, R⁴, R⁶, R⁷ and m are as defined above.

Compounds of formula XIV wherein Z is

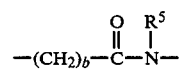

can be prepared from the reaction of a benzothiadiazine or quinazoline of formula XV with an carboxy protected ω-halo carboxylic acid (e.g. benzyl 3-bromopropionate) of formula XVI, followed by removal of the protecting group to give an acid of formula XVII:

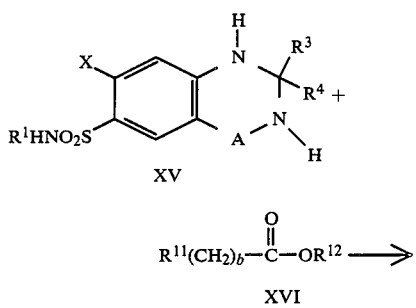

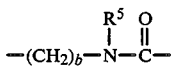

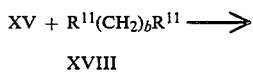

wherein A, X, $R^1$, $R^3$, $R^4$, $R^{11}$, $R^{12}$ and b are as defined above. The reaction of compounds of formula XV and XVI is preferably carried out in an inert solvent such as DMF in the presence of a base such as sodium hydride or cesium carbonate. The protecting group may be removed by conventional means, e.g. when $R^{12}$ is benzyl, by hydrogenation in the presence of a catalyst such as palladium on carbon.

The acid of formula XVII may then be treated in a manner similar to that described for compounds of formula VII to obtain compounds of formula II.

Compounds of formula XIV wherein Z is $$-(CH_2)_b-\overset{R^5}{\underset{|}{N}}-\overset{O}{\underset{\|}{C}}-$$

can be prepared by the reaction of a compound of formula XV with a di-haloalkane of formula XVIII followed by conversion of the 2-(ω-haloalkyl) compound to the corresponding amine of formula XIX:

XV + $R^{11}(CH_2)_bR^{11}$ ⟶
XVIII

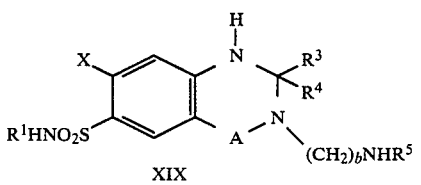

wherein $R^1$, $R^3$, $R^4$, $R^5$, $R^{11}$, A, X and b are as defined above. The reaction of the compounds of formula XV and XVIII is carried out under conditions as described above for the reaction of compounds of formula XV and XVI. The amination of the resulting 2-(ω-haloalkyl) compound is carried out in an inert solvent such as DMF using a reagent such as sodium azide or $R^5NH_2$. The azide is reduced to the corresponding amine by, for example, hydrogenation in the presence of a catalyst such as palladium on carbon. Compounds of formula XIX may be treated in a manner similar to that described for compounds of formula XI to obtain compounds of formula II.

Compounds of formulae V, VII, VIII, IX, X, XI, XV, XVI and XVIII are either known in the art or may be prepared by methods well known to those skilled in the art.

The known coupling methods above include amino group protection during the coupling reaction, for example with protecting groups such as N-formyl, N-t-butoxycarbonyl and N-carbobenzyloxy groups, followed by their removal to yield compounds of formula I. Furthermore, the $COR^8$ function wherein $R^8$ is OH may be protected by removable ester groups such as benzyl, ethyl, t-butyl and the like.

The more complex esters at $R^6$ (i.e., $R^6$ is other than hydroxy or alkoxy) are most conveniently prepared by esterifying compounds of formula I wherein $R^6$ is hydroxy and $R^8$ is a protected hydroxy, e.g. benzyloxy, with the appropriate reagent, then removing the protecting ester at $R^8$. For example, compounds of formula I wherein $R^6$ is hydroxy and $R^8$ is benzyloxy may be reacted with chloromethyl pivalate to obtain the corresponding pivaloyloxymethyl ester; the benzyl group is then removed by conventional means, e.g. hydrogenation.

The following examples further illustrate the preparation of compounds of this invention.

EXAMPLE 1

1-{N-[1(S)-Ethoxycarbonyl-5-[2-(6-chloro-3,4-dihydro-1,1-dioxo-7-sulfamoyl-1,2,4-benzothiadiazin-3-yl)acetamido]pentyl]-(S)-alanyl}-cis, syn-octahydroindole-2(S)-carboxylic acid A. Combine 3-ethoxycarbonylmethyl-6-chloro-7-sulfamoyl-3,4-dihydro-1,2,4-benzothiadiazine-1,1-dioxide (7.7 g) with ethanol (EtOH) (250 ml) and 1N sodium hydroxide (NaOH) (70 ml) for 4 hours. Concentrate to 50 ml, add 1N hydrochloric acid (HCl) (70 ml), and extract with ethyl acetate (EtOAc). Dry the EtOAc extract over anhydrous magnesium sulfate and concentrate to obtain 3-carboxymethyl-6-chloro-7-sulfamoyl-3,4-dihydro-1,2,4-benzothiadiazine-1,1-dioxide.

B. Combine the product of part A (6.0 g), 6-amino-2-(1S-t-butyloxycarbonylethylamino)hexanoic acid ethyl ester (5.1 g), and N-hydroxy benzotriazole hydrate (2.6 g) with dry dimethylformamide (DMF) (150 ml) at 0° C. Add 1-(3-dimethylaminopropyl)-3-ethyl carbodiimide hydrochloride (DCI) (3.2 g). After 3 hours, concentrate the resultant solution and partition between EtOAc and 1N sodium bicarbonate (NaHCO₃). Dry and concentrate the organic layer to obtain a crude oil (12.5 g), which can be further purified by chromatography on silica gel using chloroform:methanol:ammonia (90:9:1) to obtain N-5(S-ethoxycarbonyl-5-[1S-(t-butyloxycarbonyl)ethylamino]-pentyl-6-chloro-3,4-dihydro-1,1-dioxo-7-sulfamoyl-1,2,4-benzothiadiazine-3-acetamide.

C. Combine the product of step B (8.9 g) with HCl saturated dioxane (400 ml) for 24 hours. Decant the solution from the oil and dry the oil in vacuo to obtain N-(5(S)-ethoxycarbonyl-5-[1S-carboxyethylamino]-pentyl-6-chloro-3,4-dihydro-1,1-dioxo-7-sulfamoyl-1,2,4-benzothiadiazine-3-acetamide hydrochloride.

D. Combine the product of part C (5.8 g), triethylamine (1.8 g), 2S-benzyloxycarbonyl-S,S-perhydroindole (2.4 g), and N-hydroxybenzotriazole.H₂O (1.4 g) in dry dimethylformamide (100 ml) at 0° C., then add DCI (1.7 g). After 2 hours, concentrate and partition between EtOAc and 1N NaHCO$_3$. Dry the organic layer and evaporate the solvent in vacuo. Chromatograph the resultant residue on silica gel, eluting with chloroform:methanol:ammonia (90:9:1) to obtain 1-{N-[1(S)-ethoxycarbonyl)-5-[2-(6-chloro-3,4-dihydro-1,1-dioxo-7-sulfamoyl-1,2,4-benzothiadiazin-3-yl)acetamido]pentyl]-(S)-alanyl}-2(S)-benzyloxycarbonyl-cis,syn-octahydroindole.

E. Combine the product of part D (2.2 g) with 20% hydrogen bromide in acetic acid (50 ml) and stir 4 hours at room temperature (R.T.) Concentrate the resultant mixture, treat with diethyl ether and filter to obtain a crude solid. Chromatograph the resultant solid on AG-50W-X2 resin (hydrogen form), using 3% pyridine as eluant. Lyophilize eluate fractions to obtain a solid, and chromatograph the solid on sephadex, eluting with methanol to obtain the title compound, $[\alpha]_D^{26} = -25.6°$ (ethanol, C=0.5).

EXAMPLE 2

1-{N-[1(S)-Carboxy)-5-[2-(6-chloro-3,4-dihydro-1-1-dioxo-7-sulfamoyl-1,2,4-benzothiadiazin-3-yl)acetamido]pentyl]-(S)-alanyl}-cis, syn-octahydroindole-2(S)-carboxylic acid Combine the product of part D of Example 1 (1.8 g) with 1N NaOH (10.8 ml) and allow to stand 16 hours. Add 1N HCl (10.8 ml) to the resultant solution and filter the solid which precipitates to obtain the title compound, m.p. 205°-209° C.

EXAMPLE 3

1-{N-[1(S)-Ethoxycarbonyl-4-[2-(6-chloro-3,4-dihydro-1,1-dioxo-7-sulfamoyl-1,2,4-benzothiadiazin-3-yl)-acetamido]butyl]-(S)-alanyl}-cis, syn-octahydroindole-2(S)-carboxylic acid, hydrochloride A. Dissolve Nδ-carbobenzyloxy-(S)-ornithine, ethyl ester (49.5 g) t-butyl α-bromopropionate (75 g) and triethylamine (75 ml) in DMF (400 ml), and heat this solution at 80° for 18 hours. Cool the reaction mixture, add water (2000 ml) and extract with ether (4×400 ml). Dry the organic layer over MgSO$_4$ and concentrate the dried ether solution in vacuo. Chromatograph the resultant residue (20 g portions) on Waters Prep 500 using 4 cartridges and hexane:EtOAc (3:1) as eluant to give N-[1(S)-ethoxycarbonyl-4-(benzyloxy-carbonylamino)-butyl]-(S)-alanine, t-butyl ester and the corresponding (R)-alanine isomer.

B. Dissolve the product of step A (23.32 g) in absolute ethanol (200 ml) and water (200 ml). Add 10% palladium on charcoal (7.0 g). Hydrogenate at 50 psi for 3 hours. Filter and concentrate in vacuo to give N-[1(S)-ethoxycarbonyl-4-aminobutyl]-(S)-alanine, t-butyl ester (use immediately in next step).

C. Dissolve the product of step B (15.23 g), 3-carboxymethyl-6-chloro-3,4-dihydro-7-sulfamoyl-1,2,4-benzothiadiazine-1,1-dioxide (19.6 g), DCI (10.83 g) and 1-hydroxybenzotriazole (8.45 g) in DMF (150 ml) and stir at room temperature for 18 hours. Concentrate the reaction mixture at room temperature, add dichloromethane and concentrate. Partition the resultant residue between EtOAc and 1N NaHCO$_3$. Dry the organic layer on MgSO$_4$ and concentrate in vacuo. Chromatograph the resultant residue on silica gel (2 cartridges) using EtOAc as eluant on the Waters Prep 500 to give N-1(S)-ethoxycarbonyl-4-[2-(6-chloro-3,4-dihydro-1,1-dioxo-7-sulfamoyl-1,2,4-benzothiadiazin-3-yl)acetamido]butyl-(S)-alanine, t-butyl ester.

D. Treat the product of step C (11.0 g) with dioxane saturated with HCl gas (100 ml) and stir at room temperature for 18 hours. Concentrate in vacuo and triturate the residue with ether to give N-{1(S)-ethoxycarbonyl-4-[2-(6-chloro-3,4-dihydro-1,1-dioxo-7-sulfamoyl-1,2,4-benzothiadiazin-3-yl)acetamido]butyl}-(S)-alanine hydrochloride.

E. Treat the product of step D (6.26 g) with cis, syn-octahydroindole-2(S)-carboxylic acid benzyl ester (2.15 g), N-methyl morpholine (1.86 ml), 1-hydroxybenzotriazole (1.30 g) and DCI (2.49 g) in DMF (12 ml) at room temperature for 18 hours. Concentrate the resultant mixture in vacuo at room temperature. Add water and extract with EtOAc. Concentrate the dried (MgSO$_4$) organic solution in vacuo at room temperature. Chromatograph the resultant residue on silica gel (1 kg. 60-200 mesh) using EtOAc:absEtOH (9:1) as eluant to obtain 1-{N[1(S)-ethoxycarbonyl-4-[2-(6-chloro-3,4-dihydro-1,1-dioxo-7-sulfamoyl-1,2,4-benzothiadiazin-3-yl)acetamido]-butyl]-(S)-alanyl}-cis, syn-octahydroindole-2(S)-carboxylic acid, benzyl ester.

F. To the benzyl ester of step E, add cold 20% HBr in glacial acetic acid (20 ml), warm to room temperature and stir for 5 hours. Concentrate the reaction mixture in vacuo and triturate the residue with ether to give the corresponding hydrobromide salt.

G. Absorb the product of step F (0.70 g) on a strongly acidic ion exchange column (Bio-Rad AG 50W-X2) and elute with abs, EtOH:H$_2$O (1:4) and then with abs EtOH:H$_2$O:pyridine (77:19:4). Concentrate the desired fractions as determined by thin layer chromatography (desired product is positive to iodine). Obtain the HCl salt by adding the resultant residue to dichloromethane containing HCl gas and concentrate the resulting mixture. Chromatograph the resultant residue (20 g) on a sephadex column (170 g) using methanol as eluant to give the title compound, a white solid $[\alpha]_D^{26} -23.2°$ (MeOH).

EXAMPLE 4

1-{N-[1(S)-carboxy-4-[2-(6-chloro-3,4-dihydro-1,1-dioxo-7-sulfamoyl-1,2,4-benzothiadiazin-3-yl)-acetamido]butyl]-(S)-alanyl}-cis, syn-octahydroindole-2(S)-carboxylic acid hydrochloride To the product from Example 3 step F (0.76 g) at 0.5°, add 0.5N NaOH (15 ml), warm to room temperature (½ hour) and stir at room temperature for 18 hours. Concentrate the reaction mixture in vacuo. Treat the resultant residue in the manner described in Example 3, step G to obtain the title compound, $[\alpha]_D^{26} = -16.6°$ (MeOH).

EXAMPLE 5

1-{N-[1(S)-Ethoxycarbonyl-2-(N-(6-chloro-3,4-dihydro-1,1-dioxo-7-sulfamoyl-1,2,4-benzothiadiazin-3-yl-methyl)-carbamoyl)ethyl]-(S)-alanyl}-cis, syn-octahydroindole-2(S)-carboxylic acid A. Combine 3-aminomethyl-6-chloro-7-sulfamoyl-3,4-dihydro-benzothiadiazine-1,1-dioxide hydrochloride (1.09 g), triethylamine (0.31 g), hydroxybenzotriazole hydrate (0.46 g), and N-(t-butoxycarbonyl)-S-aspartic acid, α-ethyl ester in dry DMF (20 ml). Add DCI (0.64 g) and stir 1.5 hours. Partition the resultant mixture between water and EtOAc. Wash the organic layer with water, 1.0N NaHCO₃, then brine. Dry the organic layer over MgSO₄ and concentrate. Crystallize the resultant residue from CHCl₃—CH₃OH to obtain N-(t-butoxycarbonyl-S-aspartic acid, α-ethyl ester, β(6-chloro-7-sulfamoyl-3,4-dihydro-1,1-dioxo-1,2,4-benzothiadiazine-3-methylamide), m.p. 173° (dec).

B. Combine the product of step A (1.14 g) with 6M HCl/dioxane (10 ml). Stir 15 minutes, decant the solution, and stir the residue with ether. Filter to obtain S-aspartic acid, α-ethyl ester, β-(6-chloro-7-sulfamoyl-3,4-dihydro-1,1-dioxo-1,2,4-benzothiadiazine-3-methylamide)hydrochloride.

C. To the product of step B (0.91 g) and triethylamine (0.26 g) in EtOAc (20 ml), add a solution of t-butyl 2R-(trifluoromethanesulfonyloxy)propionate (0.71 g) in EtOAc (5 ml). Stir 3 hours and wash with water, 5% citric acid, 5% NaHCO₃, then brine. Dry the organic layer over MgSO₄ and concentrate. Chromatograph the resultant residue on silica gel eluting with 1% MeOH/EtOAc to obtain N-(1S-t-butoxycarbonylethyl)-S-aspartic acid, α-ethyl ester, β-(6-chloro-7-sulfamoyl-3,4-dihydro-1,1-dioxo-1,2,4-benzothiadiazine-3-methylamide), $[\alpha]_D^{26} = -19.4°$ (EtOH, C=0.5).

D. Combine the product of step C (0.90 g) with 10 ml 6M HCl/dioxene and anisole (1.6 g). Let stand 24 hours and decant the solution. Triturate with ether and filter to obtain N-(1S-carboxyethyl)-S-aspartic acid, α-ethyl ester, β-(6-chloro-7-sulfamoyl-3,4-dihydro-1,1-dioxo-1,2,4-benzothiadiazine-3-methylamide)hydrochloride.

E. To the product of step D (0.58 g), triethylamine (0.20 g), hydroxybenzotriazole hydrate (0.15 g) and benzyl S,S,S-perhydroindole-2-carboxylate (0.26 g) in dry DMF (10 ml), add DCI (0.19 g). After 2 hours, concentrate and partition between EtOAc and 1N NaHCO₃. Wash with water, then brine. Dry the organic layer over MgSO₄ and concentrate. Chromatograph the resulting residue on silica gel with 9:1 CHCl₃—CH₃OH to obtain benzyl 1-{N-[1S-ethoxycarbonyl-2-(N-(6-chloro-3,4-dihydro-1,1-dioxo-7-sulfamoyl-1,2,4-benzothiadiazin-3-yl-methyl)carbamoyl)ethyl)-S-alanyl}cis, syn-octahydroindole-2S-carboxylate, $[\alpha]_D^{26} = -3.5°$ (EtOH, c=1)

F. Hydrogenate the product of step E (0.33 g) in ethanol (70 ml) with 0.07 g 10% Pd/C at 1 atm. until uptake of 0.40 mmole hydrogen. Filter and concentrate the filtrate to obtain the title compound as a solid.

EXAMPLE 6

1-{N-(1S-Ethoxycarbonyl-5-(N-(6-chloro-3,4-dihydro-1,1-dioxo-7-sulfamoyl-1,2,4-benzothiadiazin-2-yl)acetamido)-pentyl]-S-alanyl}-cis, syn-octahydroindole-2(S)-carboxylic acid A. To 6-chloro-3,4-dihydro-1,1-dioxo-7-sulfamoyl-1,2,4-benzothiadiazine (6.0 g) in dry DMF (50 ml). Add Cs₂CO₃ (3.26 g=10 mmol) and benzyl bromoacetate (4.58 g) and stir 18 hours. Pour into water, extract with ethyl acetate, and wash with water. Dry the organic layer over MgSO₄ and concentrate. Chromatograph the resultant residue on silica gel with 10:1 CHCl₃-MeOH to obtain benzyl(6-chloro-3,4-dihydro-1,1-dioxo-7-sulfamoyl-1,2,4-benzothiadiazin-2-yl)acetate.

B. Combine the product of step A (0.44 g) with 0.07 g 10% Pd/C in THF (50 ml). Hydrogenate at 1 atm until uptake of 1.0 eq. hydrogen. Filter and concentrate the filtrate to obtain (6-chloro-3,4-dihydro-1,1-dioxo-7-sulfamoyl-1,2,4benzothiadiazin-2-yl)acetic acid as a foam.

C. Treat the product of step B in a manner similar to that described in Example 1, step B to obtain the corresponding 1,2,4-benzothiadiazin-2-acetamide.

D. Treat the product of step C in a manner similar to that described in Example 1, step C to obtain the corresponding hydrochloride.

E. Treat the product of step D in a manner similar to that described in Example 1, step D to obtain 1-N-{N-[1(S)-ethoxycarbonyl)-5-[N-(6-chloro-3,4-dihydro-1,1-dioxo-7-sulfamoyl-1,2,4-benzothiadiazin-2-yl)acetamido]-pentyl]-(S)-alanyl}-2(S)-benzyloxycarbonyl-cis, syn-octahydroindole.

F. Treat the product of step E with HBr as described in Example 1 step E to obtain the title compound.

EXAMPLE 7

1-{N-(1S-ethoxycarbonyl-2-(N-2-(6-chloro-3,4-dihydro-1,1-dioxo-7-sulfamoyl-1,2,4-benzothiazin-2-yl)ethyl)carbamoyl)-ethyl]-S-alanyl}-cis, syn-octahydroindole-2S-carboxylic acid A. Treat 6-chloro-3,4-dihydro-1,1-dioxo-7-sulfamoyl-1,2,4-benzothiadiazine with Cs₂CO₃ and substitute 1,2-dibromoethane for benzylbromoacetate in the procedure of Example 6, step A to obtain 2-(2-bromoethyl)-6-chloro-3,4-dihydro-1,1-dioxo-7-sulfamoyl-1,2,4-benzothiadiazine.

B. Combine the product of step A (12.2 g) with sodium azide (3.9 g) in DMF (200 ml). Stir 44 hours, extract with ethyl acetate, wash with water, dry the organic layer over MgSO₄ and concentrate. Dissolve the resultant residue in ethanol (150 ml), add 5.0 g 10Pd/C and hydrogenate at 3 atm for 4 hours. Filter and concentrate the filtrate to obtain 2-(2-aminoethyl)-6-chloro-3,4-dihydro-1,1-dioxo-7-sulfamoyl-1,2,4-benzothiadiazine.

C. Treat the product of step B with N-(t-butoxycarbonyl)-S-aspartic acid, α-ethyl ester as described in Example 5, step A, and continue the procedure described in Example 5, steps B through F to obtain the title compound.

Using the methods described above and substituting appropriate reagents, the compounds described in the following tables are prepared.

TABLE 1

FORMULA I

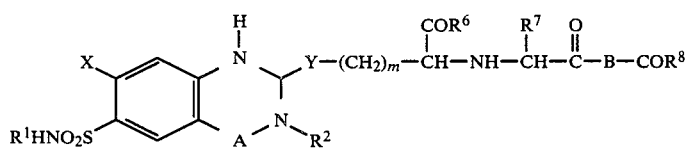

| A | B | p | q | n | Y | X | R¹ | R² | R⁶ | R⁷ | R⁸ | m |
|---|---|---|---|---|---|---|---|---|---|---|---|---|
| SO₂ | IIIa | — | — | — | —(CH₂)₂CONH— | CF₃ | CH₃ | H | —OCH₂CH₃ | CH₃ | OH | 4 |

TABLE 1-continued
FORMULA I

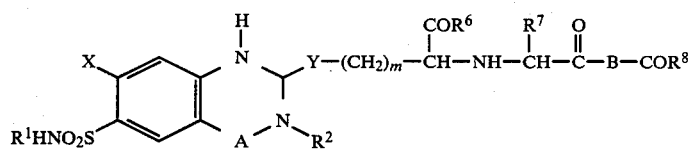

| A | B | p | q | n | Y | X | R¹ | R² | R⁶ | R⁷ | R⁸ | m |
|---|---|---|---|---|---|---|---|---|---|---|---|---|
| SO$_2$ | IIIc | 1 | 1 | — | —CH$_2$CON(CH$_3$)— | Cl | H | CH$_3$ | OH | H | OH | 3 |
| SO$_2$ | IIId | 1 | 1 | 0 | —CH$_2$CONH— | Cl | CH$_3$ | H | —OCH$_2$CH$_3$ | CH$_3$ | OH | 4 |
| SO$_2$ | IIIa | — | — | — | —CH$_2$NHCO— | Cl | H | H | —OCH$_3$ | CH$_3$ | OCH$_3$ | 3 |
| SO$_2$ | IIIc | 1 | 1 | — | —CH$_2$—N(CH$_3$)CO— | CF$_3$ | H | φ | OH | CH$_3$ | OH | 4 |
| SO$_2$ | IIId | 1 | 1 | 0 | —(CH$_2$)$_3$NHCO— | Cl | CH$_2$CH$_3$ | —CH$_2$CH$_3$ | OH | —(CH$_2$)$_4$NH$_2$ | OH | 3 |
| CO | IIIa | — | — | — | —CONH— | Cl | CH$_3$ | H | —OCH$_2$CH$_3$ | CH$_3$ | OH | 3 |
| CO | IIIb | 0 | 1 | — | —CON(CH$_3$)— | CF$_3$ | H | —CH$_2$φ | OH | —(CH$_2$)$_4$NH$_2$ | OH | 2 |
| CO | IIIc | 0 | 1 | — | —(CH$_2$)$_4$CON(φ)— | Cl | CH$_3$ | CH$_3$ | OH | CH$_3$ | OH | 2 |
| CO | IIId | 1 | 1 | 0 | —(CH$_2$)$_2$CON(CH$_2$φ)— | CF$_3$ | CH$_2$CH$_3$ | H | —OCH$_2$CH$_3$ | CH$_3$ | OCH$_3$ | 4 |
| CO | IIIa | — | — | — | —CH$_2$NHCO— | Cl | H | -φ | OH | —CH$_2$CH$_3$ | OH | 1 |
| CO | IIIb | 0 | 1 | — | —(CH$_2$)$_4$N(CH$_2$φ)CO— | Cl | CH$_3$ | H | OH | CH$_3$ | —OCH$_2$CH$_3$ | 3 |
| CO | IIIc | 1 | 1 | — | —(CH$_2$)$_2$NφCO— | CF$_3$ | CH$_3$ | CH$_3$ | —OCH$_2$CH$_3$ | —(CH$_2$)$_3$NH$_2$ | OH | 4 |
| CO | IIId | 1 | 1 | 0 | —(CH$_2$)N(CH$_3$)CO— | Cl | CH$_3$ | CH$_3$ | OH | H | OH | 1 |
| SO$_2$ | IIIb | 1 | 0 | — | —CH$_2$CONH— | Cl | H | H | OH | CH$_3$ | OH | 1 |
| SO$_2$ | IIIb | 1 | 1 | — | —CH$_2$N(φ)CO— | Cl | CH$_3$ | CH$_3$ | —OCH$_2$CH$_3$ | CH$_3$ | OH | 4 |
| CO | IIIb | 2 | 0 | — | —(CH$_2$)$_2$CON(CH$_3$)— | CF$_3$ | H | H | OH | CH$_3$ | OH | 3 |
| CO | IIIb | 0 | 2 | — | —(CH$_2$)$_6$NHCO— | Cl | CH$_3$ | CH$_3$ | OH | H | OH | 1 |
| SO$_2$ | IIIc | 1 | 0 | — | —(CH$_2$)$_3$CON(CH$_2$φ)— | Cl | CH$_3$ | CH$_3$ | OH | CH$_3$ | OH | 3 |
| SO$_2$ | IIIc | 1 | 1 | — | —CH$_2$N(CH$_3$)CO— | CF$_3$ | H | H | —OCH$_2$CH$_3$ | —(CH$_2$)$_4$NH$_2$ | OH | 4 |
| CO | IIIc | 2 | 0 | — | —CONH— | Cl | CH$_3$ | CH$_3$ | OH | CH$_3$ | OH | 3 |
| CO | IIIc | 0 | 2 | — | —(CH$_2$)$_4$N(CH$_3$)CO— | Cl | H | H | OH | H | OH | 2 |
| SO$_2$ | IIId | 1 | 0 | 0 | —(CH$_2$)$_6$CON(CH$_2$φ)— | Cl | CH$_3$ | —CH$_2$φ | OH | CH$_3$ | OH | 4 |
| SO$_2$ | IIId | 1 | 0 | 1 | —CH$_2$NHCO— | Cl | H | H | OH | H | OH | 1 |
| CO | IIId | 2 | 0 | 0 | —CH$_2$NHCO— | Cl | H | H | —OCH$_3$ | CH$_3$ | OH | 3 |
| CO | IIId | 2 | 0 | 1 | —CONH— | Cl | H | H | OH | —CH$_2$CH$_3$ | OH | 4 |

TABLE 2
FORMULA II $$R^1HNO_2S-\underset{X}{\underset{|}{C_6H_3}}-\overset{H}{\underset{|}{N}}-\underset{R^4}{\overset{R^3}{C}}-\underset{A}{N}-Z-(CH_2)_m-\overset{COR^6}{\underset{|}{CH}}-NH-\overset{R^7}{\underset{|}{CH}}-\overset{O}{\underset{||}{C}}-B-COR^8$$

| A | B | p | q | n | Z | X | R¹ | R³,R⁴ | R⁶ | R⁷ | R⁸ | m |
|---|---|---|---|---|---|---|----|-------|----|----|----|----|
| SO₂ | IIIa | — | — | — | —(CH₂)₂CON(CH₃)— | Cl | CH₃ | H,CH₃ | OH | CH₃ | OH | 3 |
| SO₂ | IIIc | 1 | 1 | — | —CH₂CON(φ)— | Cl | H | CH₃,CH₃ | —OCH₂CH₃ | H | OCH₂CH₃ | 4 |
| SO₂ | IIId | 1 | 1 | 0 | —(CH₂)₆CON(CH₃φ)— | Cl | —CH₂CH₃ | H,φ | OCH₃ | —(CH₃)₄NH₂ | OH | 2 |
| SO₂ | IIIa | 1 | — | — | —(CH₂)₂N(CH₂CH₃)CO— | CF₃ | H | H,—CH₂φ | OH | —CH₂CH₃ | OCH₂CH₃ | 4 |
| SO₂ | IIIc | 1 | — | 0 | —(CH₂)₂Nφ CO— | Cl | CH₃ | H,H | OH | CH₃ | OH | 1 |
| SO₂ | IIId | — | 1 | — | —(CH₂)₃N(CH₂CH₂φ)CO— | Cl | —CH₂CH₃ | H,H | —OCH₂CH₃ | CH₃ | OH | 4 |
| SO₂ | IIIa | — | — | — | —(CH₂)₂NHCO— | Cl | CH₃ | —(CH₂)₄— | OH | H | OH | 4 |
| CO | IIIb | — | 1 | 0 | —(CH₂)₃N(φ)CO— | Cl | H | H,H | OH | CH₃ | OH | 3 |
| CO | IIId | 0 | — | — | —(CH₂)₂N(CH₂φ)CO— | Cl | CH₃ | H,CH₃ | OH | —(CH₃)₄NH₂ | OCH₃ | 2 |
| CO | IIIa | 0 | 1 | — | —(CH₂)₆N(CH₂CH₃)CO— | CF₃ | H | H,H | OCH₂CH₃ | CH₃ | OH | 1 |
| CO | IIIc | 1 | — | 0 | —(CH₂)₂CONH— | Cl | CH₃ | —(CH₂)₆— | OH | CH₃ | OCH₃ | 4 |
| CO | IIId | 0 | — | — | —CH₂CONH— | CF₃ | H | H,—CH₂CH₃ | OH | H | OH | 2 |
| SO₂ | IIIc | 0 | 1 | — | —(CH₂)₃CON(CH₂CH₂φ)— | Cl | CH₃ | H,H | OH | CH₃ | OH | 3 |
| SO₂ | IIId | 1 | — | 0 | —CH₂CON(CH₂CH₂φ)— | Cl | H | —CH₂CH₃,—CH₂CH₃ | —OCH₂CH₃ | CH₃ | OH | 4 |
| CO | IIIb | 1 | — | — | —CH₂CON(CH₂φ)— | CF₃ | —CH₂CH₃ | H,H | OH | CH₃ | OH | 2 |
| CO | IIIb | 2 | — | — | —(CH₂)₂NHCO— | Cl | H | H,—CH₂φ | OH | H | OH | 3 |
| SO₂ | IIIb | 0 | 0 | — | —(CH₂)₆CON(CH₂CH₃)— | Cl | CH₃ | —(CH₂)₅— | OH | —(CH₃)₄NH₂ | OH | 4 |
| CO | IIIc | 1 | 2 | — | —(CH₂)₃N(CH₃)CO— | Cl | CH₃ | H,H | OH | CH₃ | OH | 4 |
| SO₂ | IIId | 1 | 0 | — | —CH₂NH— | Cl | CH₃ | CH₃,CH₃ | OH | CH₃ | OH | 3 |
| SO₂ | IIIc | 2 | 1 | — | —(CH₂)₃N(CH₃)CO— | Cl | H | H,φ | —OCH₂CH₃ | H | —OCH₂CH₃ | 2 |
| CO | IIIc | 2 | 0 | — | —(CH₂)₂CON(φ)CO— | CF₃ | CH₃ | —(CH₂)₄— | OH | CH₃ | OH | 4 |
| SO₂ | IIId | 1 | — | 0 | —CH₂CON(CH₃)— | Cl | CH₃ | H,H | OH | H | OH | 3 |
| SO₂ | IIId | — | 0 | 1 | —(CH₂)₂NHCO— | Cl | H | H,H | OH | CH₃ | —OCH₂CH₃ | 2 |
| CO | IIId | 2 | 0 | — | —(CH₂)₃NHCO— | Cl | CH₃ | —(CH₂CH₃,—CH₂CH₃) | —OCH₂CH₃ | —(CH₃)₄NH₂ | OH | 3 |
| CO | IIId | — | 0 | 1 | —(CH₂)₈NHCO— | Cl | H | H,H | OH | CH₃ | OH | 1 |

The compounds of this invention are useful in view of their pharmacological properties. In particular, they possess activity as anithypertensive agents, as evidenced by their ability to reduce blood pressure in mammals in which the blood pressure has become abnormally elevated. Compounds of this invention also show activity as diuretic agents.

Since these compounds are believed to act as angiotensin converting enzyme inhibitors, it is also contemplated that they may be used in treating other cardiovascular disorders, for example congestive heart failure, in the same manner as other ACE inhibitors such as captopril and enalapril may be used.

The compounds of this invention can be combined with pharmaceutical carriers and administered in a variety of well-known pharmaceutical forms suitable for oral or paranteral administration to provide compositions useful in the treatment of cardiovascular disorders and particularly mammalian hypertension.

The daily antihypertensive dose of the compounds of this invention will typically be in the range of about 1 to about 25 mg/kg, of mammalian weight, administered in single or divided doses. The exact dose to be administered is determined by the attending clinician and is dependent upon the potency of the administered compound, i.e. where the particular compound lies within the above range, as well as upon the age, weight and condition of the individual.

Generally, in treating humans having hypertension, the compounds of this invention may be administered to patients in need of such treatment in a dosage range of about 5 to about 500 mg per patient generally given several times a day, thus giving a total daily dose of from about 5 to about 2000 mg per day.

The antihypertensive compositions containing the compounds of this invention will preferably contain from about 5 to about 250 mg of the active compound per dosage unit.

The compositions of the present invention are most preferably administered orally. Typical formulations for oral administration are those such as tablets, capsules, syrups, elixirs or suspensions. Typical injectable formulations include solutions and suspensions. Also contemplated are mechanical delivery systems, e.g. transdermal dosage forms.

The typical acceptable pharmaceutical carriers for use in the formulations described above are exemplified by: sugars such as lactose, sucrose, mannitol and sorbitol; starches such as corn starch, tapioca starch and potato starch; ceullulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic sufactants; ethylene gylcol polymers; beta-cyclodextrin; fatty alcohols and hydrolyzed cereal solids; as well as other non-toxic compatible fillers, binders, disintegrants, buffers, preservatives, anti-oxidants, lubricants, flavoring agents, and the like commonly used in pharmaceutical formulations.

In the following examples, the "active ingredient" is 1-N-N-[1(S)-ethoxycarbonyl-5-[2-(6-chloro-3,4-dihydro-1,1-dioxo-7-sulfamoyl-1,2,4-benzothiadiazin-3-yl)acetamido]pentyl-(S)-alanyl -cis,syn-octahydro-1Hindole-2-(S) -carboxylic acid. It is contemplated, however, that this compound may be replaced by equally effective quantities of other compounds within the scope of formulae I or II.

EXAMPLE 8

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium stearate | 2.0 | 1.0 |
| | 500.0 | 250.0 |

Blend the active ingredient, lactose, and corn starch until uniform; then blend the magnesium stearate into the resulting powder. Encapsulate the mixture into suitably sized two-piece hard gelatin capsules.

EXAMPLE 9

| Tablet | Amount (mg) | |
|---|---|---|
| Active Ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill te dried granules through a suitable milling machine using a 16 mesh stainless steel screen. Blend in the magnesium stearate and compress the resulting mixture into tablets of desired shape, thickness, hardness and disintegration.

EXAMPLE 10

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–25° C. Charge and dissolve all other excipients and the active ingredient. Bring the solution to final volume, filter it through a sterilizing membrane and fill into sterile containers.

Similarly, substitute other compounds of the present invention to prepare other compositions of the present invention.

We claim:

1. A compound represented by the formulae

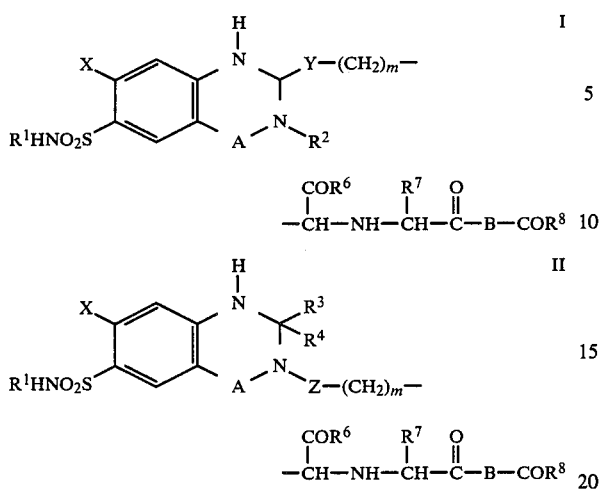

wherein
A is —SO₂—
X is Cl or CF₃;
Y is

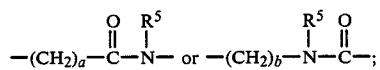

Z is

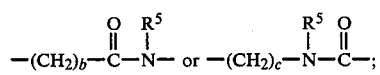

B is

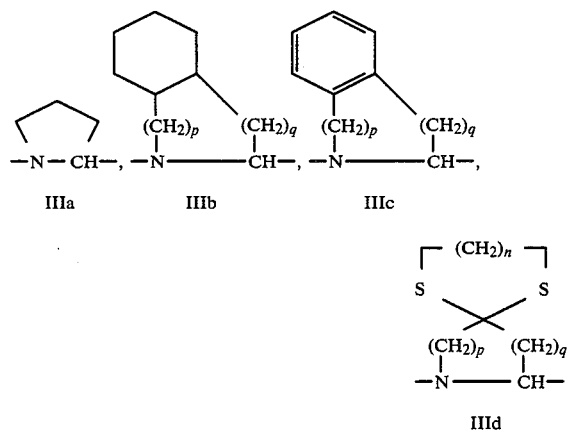

$R^1$ is hydrogen or lower alkyl;
$R^2$ and $R^5$ are independently hydrogen, lower alkyl, phenyl, or phenyl(lower)alkyl;
$R^3$ and $R^4$ are independently hydrogen, lower alkyl, halo lower alkyl, phenyl, or phenyl(lower)alkyl, or $R^3$ and $R^4$ taken together with the carbon to which they are attached can form a 5–7 membered cycloalkyl ring;
$R^6$ and $R^8$ are independently hydroxy, alkoxy having from 1 to 8 carbon atoms, L—$Q_r$—$(CH_2)_s$—O—, wherein L is phenyl, substituted phenyl, 1-naphthyl or 2-naphthyl; Q is oxygen or sulfur; r is 0 or 1 and s is 0 to 4; and wherein the substituents on the substituted phenyl are chosen from group M, wherein M is halogen, hydroxy, trifluoromethyl, alkoxy having from 1 to 6 carbon atoms, alkyl from 1 to 6 carbon atoms, 2-furanyl, 3-furanyl, 2-thienyl, 3-thienyl, and phenyl (which phenyl may be substituted with halogen, hydroxy, trifluoromethyl, alkoxy having from 1 to 6 carbon atoms or alkyl having from 1 to 6 carbon atoms), provided that when s is zero, r is zero; —OCH₂OCO—alkyl wherein the alkyl has from 3 to 8 carbon atoms, —OCH₂CO—phenyl, wherein the phenyl may be substituted with group M, 1-gylceryl,

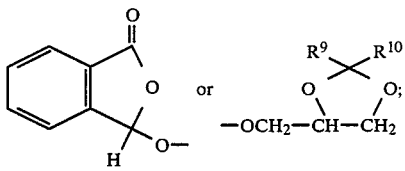

$R^7$ is hydrogen, lower alkyl, or aminoloweralkyl;
$R^9$ is hydrogen, lower alkyl, phenyl, or phenyl substituted by group M;
$R^{10}$ is hydrogen or lower alkyl;
a is 0–8;
b is 1–8;
c is 2–8;
m is 1–4;
n is 0 or 1;
p and q are each 0,1 or 2, provided that in formulae IIIb and IIIc the sum of p and q is 1 or 2, and that in formula IIId p is not 0; and pharmaceutically acceptable salts thereof.

2. A compound of claim 1 wherein B is represented by formula IIIa.

3. A compound of claim 1 wherein B is represented by formula IIIb.

4. A compound of claim 3 wherein p is 0 and q is 1.

5. A compound of claim 1 wherein B is represented by formula IIIc.

6. A compound of claim 5 wherein p and q are each 1.

7. A compound of claim 1 wherein B is represented by formula IIId.

8. A compound of claim 7 wherein p and q are each 1 and n is 0.

9. A compound of claim 4 which is 1-{N-[1(S)-ethoxycarbonyl-5-[2-(6-chloro-3,4-dihydro-1,1-dioxo-7-sulfamoyl-1,2,4-benzothiadiazin-3-yl)acetamido]-pentyl]-(S)-alanyl}-cis, syn-octahydroindole-2(S)-carboxylic acid.

10. A compound of claim 4 which is 1-{N-[1 (S)-carboxy)-5[2-(6-chloro-3,4-dihydro-1,1-dioxo-7-sulfamoyl-1,2,4-benzothiadiazin-3yl)acetamido]pentyl]-(S)-alanyl}-cis, syn-octahydroindole-2(S)carboxylic acid.

11. A compound of claim 4 which is 1-{N-[1(S)-ethoxycarbonyl-4-[2-(6-chloro-3,4-dihydro-1,1-dioxo-7-sulfamoyl-1,2,4-benzothiadiazin-3-yl)acetamido]-butyl]-(S)-alanyl}-cis, syn-octahydroindole-2(S)-carboxylic acid.

12. A compound of claim 4 which is 1-{N-1(S)-carboxy-4-[2-(6-chloro-3,4-dihydro-1,1-dioxo-7-sulfamoyl-1,2,4-benzothiadiazin-3-yl)acetamido]-butyl]-(S)-alanyl}-cis, syn-octahydroindole-2(S)-carboxylic acid.

13. A compound of claim 4 which is 1-{N-[1(S)-ethoxycarbonyl-2-(N-(6-chloro-3,4-dihydro-1,1-dioxo-7-sulfamoyl-1,2,4-benzothiadiazin-2-yl-methyl)-carbamoyl)ethyl]-(S)-alanyl}-cis, syn-octahydroindole-2(S)-carboxylic acid.

14. A compound of claim 4 which is 1-{N-(1(S)-ethoxycarbonyl-2-(N-2-(6-chloro-3,4-dihydro-1,1-dioxo-7-sulfamoyl-1,2,4-benzothiadiazin-2-yl)ethyl)-carbamoyl)-ethyl]-S-alanyl}-cis, syn-octahydroindole-2(S)-carboxylic acid.

15. A compound of claim 4 which is 1-{N-(1(S)-carboxy-2-(N-2-(6-chloro-3,4-dihydro-1,1-dioxo-7-sulfamoyl-1,2,4-benzothiadiazin-2yl)ethyl)-carbamoyl)-ethyl]-S-alanyl}-cis, syn-octahydroindole-2(S)-carboxylic acid.

16. A compound of claim 4 which is 1-{N-(1(S)-carboxy-2-(N-(6-chloro-3,4-dihydro-1,1-dioxo-7-sulfamoyl-1,2,4-benzothiadiazin-2-yl)methyl)-carbamoyl)-ethyl]-S-alanyl}-cis, syn-octahydroindole-2(S)-carboxylic acid.

17. A pharmaceutical composition comprising an antihypertensive effective amount of a compound according to claim 1 together with a pharmaceutically acceptable carrier.

18. A method of treating hypertension in mammals comprising administering to a hypertensive mammal an antihypertensive effective amount of a compound of claim 1.

* * * * *